United States Patent
Steinle et al.

(10) Patent No.: US 11,642,428 B2
(45) Date of Patent: May 9, 2023

(54) STERILITY-PRESERVING ROBOTIC FRONTEND-SYSTEM

(71) Applicant: Brainlab AG, Munich (DE)

(72) Inventors: Wolfgang Steinle, Munich (DE); Nils Frielinghaus, Heimstetten (DE); Stefan Hofberger, Munich (DE)

(73) Assignee: Brainlab AG, Munich (DE)

( * ) Notice: Subject to any disclaimer, the term of this patent is extended or adjusted under 35 U.S.C. 154(b) by 1259 days.

(21) Appl. No.: 16/081,167

(22) PCT Filed: Apr. 19, 2017

(86) PCT No.: PCT/EP2017/059282
§ 371 (c)(1),
(2) Date: Aug. 30, 2018

(87) PCT Pub. No.: WO2018/192648
PCT Pub. Date: Oct. 25, 2018

(65) Prior Publication Data
US 2021/0178002 A1    Jun. 17, 2021

(51) Int. Cl.
*A61B 34/30*    (2016.01)
*A61L 2/26*    (2006.01)
*A61B 34/00*    (2016.01)

(52) U.S. Cl.
CPC .............. *A61L 2/26* (2013.01); *A61B 34/25* (2016.02); *A61B 34/30* (2016.02); *A61L 2202/24* (2013.01)

(58) Field of Classification Search
CPC ......... A61B 90/50; A61B 34/30; A61B 90/57; B25J 9/0075
See application file for complete search history.

(56) References Cited

U.S. PATENT DOCUMENTS

| | | | | |
|---|---|---|---|---|
| 5,413,573 A | * | 5/1995 | Koivukangas | A61B 90/50 606/1 |
| 2006/0161136 A1 | * | 7/2006 | Anderson | A61B 34/71 606/1 |

(Continued)

FOREIGN PATENT DOCUMENTS

| | | |
|---|---|---|
| WO | 2015030671 A1 | 3/2015 |
| WO | 2016134266 A1 | 8/2016 |

(Continued)

OTHER PUBLICATIONS

European Patent Office, International Search Report and Written Opinion, corresponding PCT/EP2017/059282 dated Jan. 8, 2018, pp. 1-13.

*Primary Examiner* — Martin T Ton
(74) *Attorney, Agent, or Firm* — Tucker Ellis LLP

(57) ABSTRACT

A sterility-preserving robotic frontend-system, including a flexible trajectory-guide including at least one force- and/or torque-transmitting coupling-member, a baffle-member separating a sterile section from a non-sterile section, and a sterility-sleeve attached to the baffle-member; an actuator unit having a sensor unit that senses at least one of a) whether a trajectory-guide is placed with respect to the actuator unit in a manner that allows engaging-members to accurately engage an actuator interface, and b) whether the engaging-members have accurately engaged the actuator-interface; and a retainer-receptacle adapted to temporarily accommodate the trajectory guide, and to restrain flexibility of the trajectory-guide while it is accommodated. A packaging-container having an inner sterile volume containing the retainer-receptacle and the trajectory-guide and a method of setting up such a sterility-preserving robotic frontend-system.

6 Claims, 6 Drawing Sheets

(56) References Cited

U.S. PATENT DOCUMENTS

| | | |
|---|---|---|
| 2006/0161138 A1 | 7/2006 | Orban, III et al. |
| 2010/0234856 A1* | 9/2010 | Stoianovici ............ A61B 90/11 |
| | | 606/130 |
| 2015/0202009 A1* | 7/2015 | Nussbaumer .......... A61B 46/27 |
| | | 128/856 |
| 2015/0374445 A1* | 12/2015 | Gombert .............. B25J 19/0075 |
| | | 606/130 |
| 2016/0242861 A1 | 8/2016 | Flatt et al. |
| 2016/0249991 A1 | 9/2016 | Glozman et al. |
| 2018/0116753 A1* | 5/2018 | Hofberger ............... A61B 90/50 |
| 2018/0125597 A1* | 5/2018 | Gogarty ................. A61B 90/05 |

FOREIGN PATENT DOCUMENTS

| | | |
|---|---|---|
| WO | 2016164266 A2 | 10/2016 |
| WO | 2017064050 A1 | 4/2017 |

\* cited by examiner

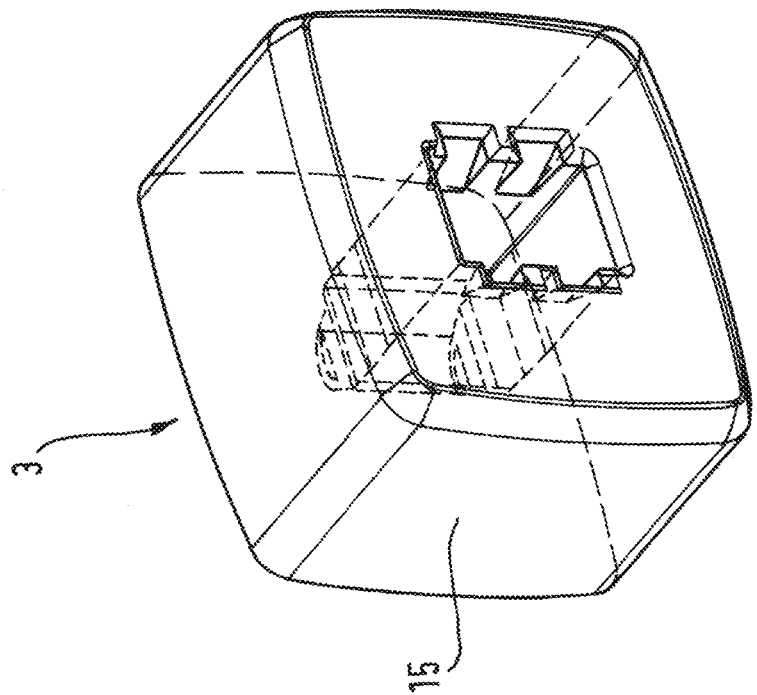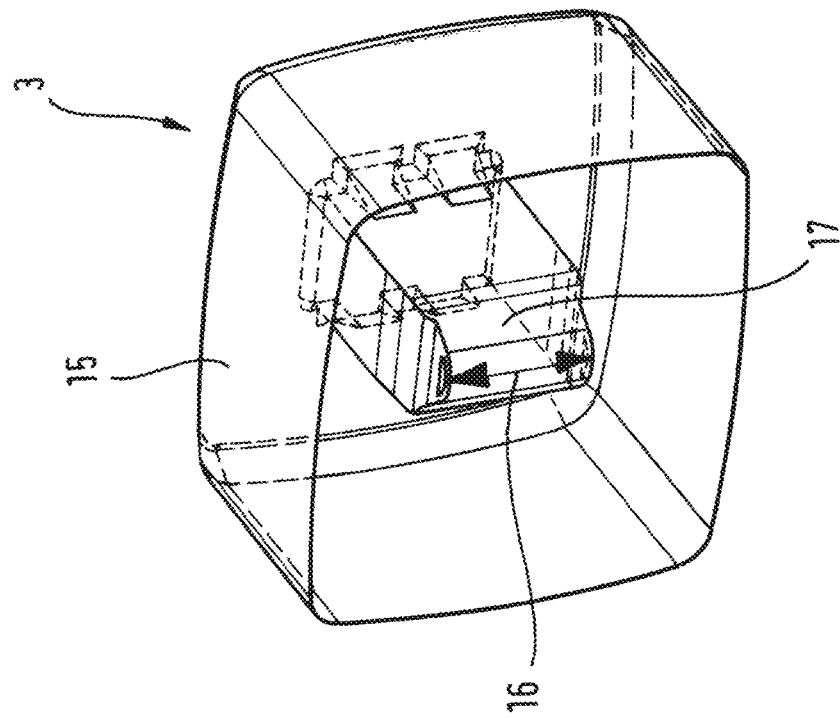

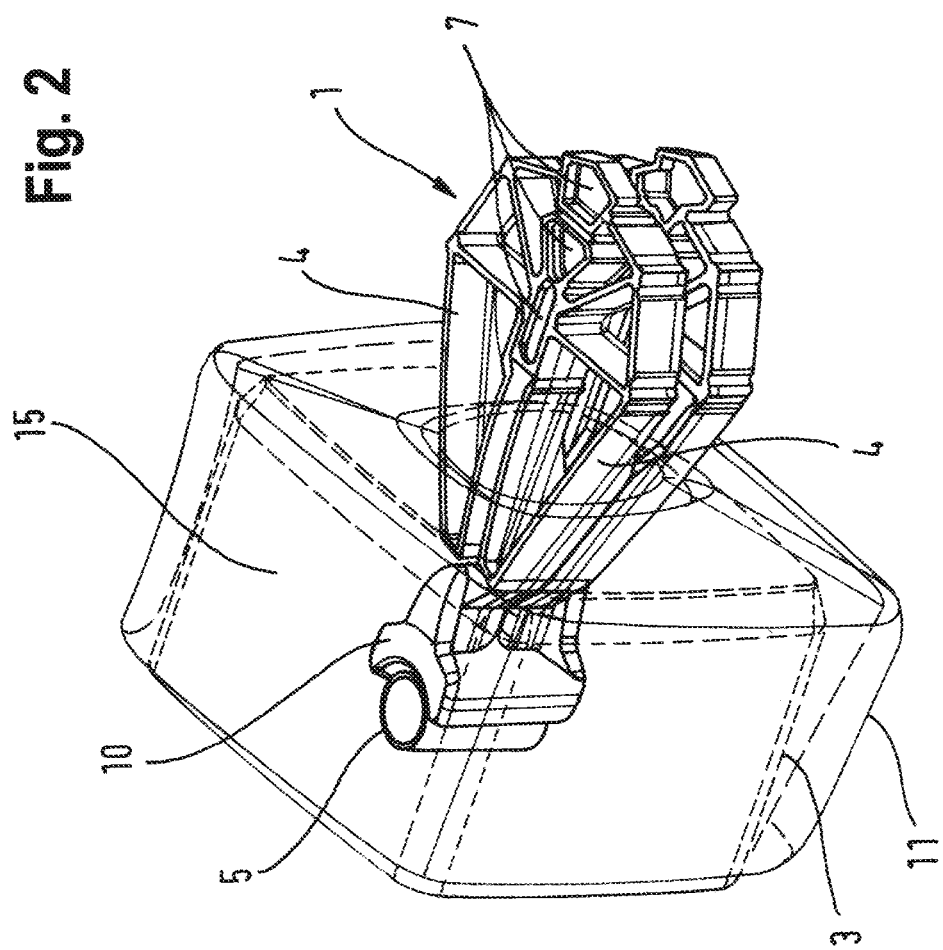

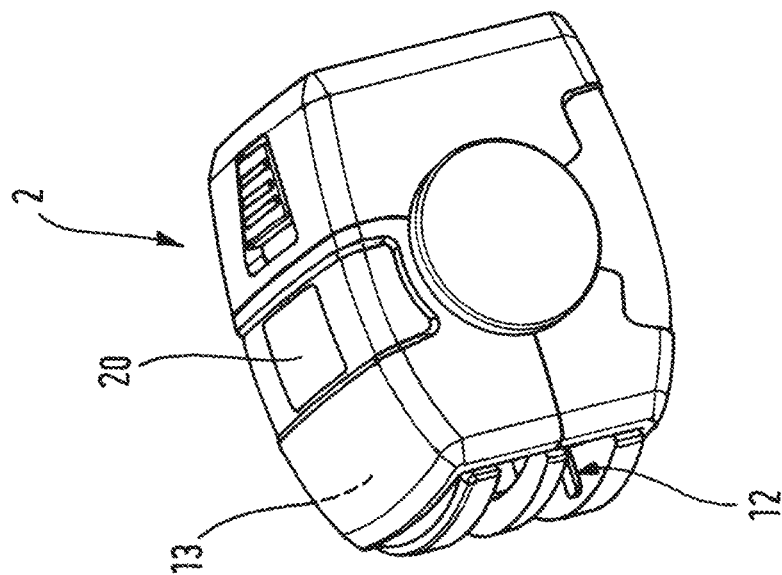
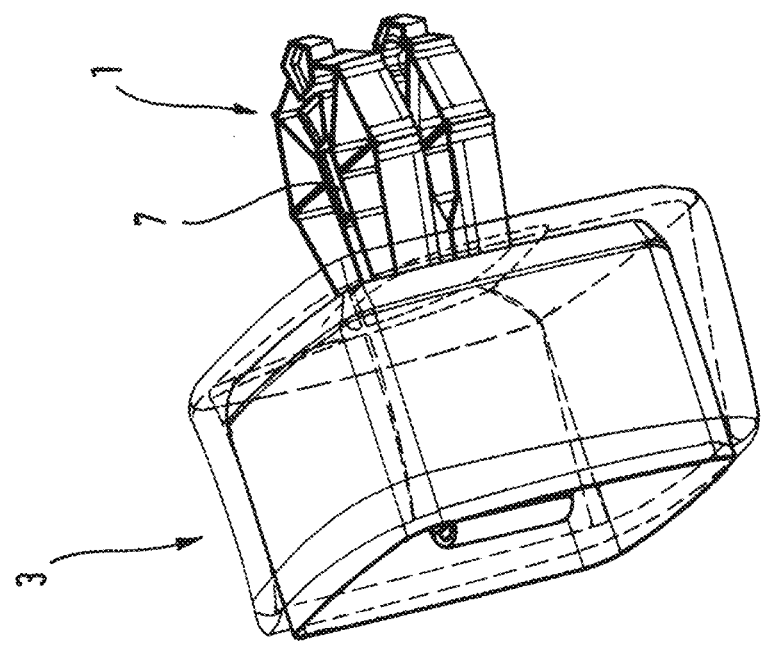

STERILITY-PRESERVING ROBOTIC FRONTEND-SYSTEM

RELATED APPLICATION DATA

This application is a national phase application of International Application No. PCT/EP2017/059282 filed Apr. 19, 2017.

TECHNICAL FIELD

The present invention relates to a robotic frontend-system which may be utilized during a medical procedure to hold and guide an elongated medical instrument to a target region within a patient body to be treated.

SUMMARY

In medical procedures which require an elongated medical instrument such as a needle, a stimulation lead, a biopsy needle or a probe to be advanced through tissue along a predefined trajectory to a target region, trajectory-guides are widely used. Such trajectory-guides are usually connected to a support structure, such as a stereotactic arc, which holds the elongated instrument precisely rigidly to the support structure and therefore also to the patient, so that the instrument can be moved along its longitudinal axis only. The support structure is adjusted by a medical personnel so that the longitudinal axis of the elongated instrument conforms to the planned trajectory which runs through the target region. After fixing the support structure in the correct position, the elongated instrument is then advanced to the target region. For an accurate placement of the elongated instrument the longitudinal axis of the instrument has to be matched precisely to the planned trajectory, which requires a difficult and time consuming adjustment procedure of a support structure such as a stereotactic arc.

Prior art documents US 2006/161138 A1, US 2015/202009 A1, WO 2016/164266 A1 and PCT/EP2016/074320 each show robotic frontend-systems for the aforementioned purpose. Such systems generally consist of reusable unsterile parts and sterile parts which reach into the sterile operation field around the patient who is to be treated. For setting up the robotic system, an interaction is needed to connect the sterile parts to the reusable unsterile parts including the support arm. As sterility has to be preserved at all costs, known approaches for setting up these robotic systems are complicated and time consuming.

Thus, there is a need for an approach that provides a fast and easy setup without compromising sterility. The present invention provides such an approach.

The invention is defined by the appended independent claims. Advantages, advantageous features, advantageous embodiments and advantageous aspects of the present invention are disclosed in the following and contained in the subject matter of the dependent claims. Different advantageous features can be combined in accordance with the invention wherever technical expedient and feasible. Specifically, a feature of one embodiment which has the same or a similar function to another feature of another embodiment can be exchanged with said other feature, and a feature of one embodiment which adds an additional function to another embodiment can in particular be added to said another embodiment.

The sterility-preserving robotic frontend-system according to the present invention includes:

- a flexible trajectory-guide comprising at least one pair of force- and/or torque-transmitting coupling-members that act, in an opposed manner, on an instrument-interface adapted to hold a medical instrument, thereby adjustably coupling the instrument-interface to an actuator-interface adapted to be releasably engaged and held by an actuator unit at two or more separate locations which are movable with respect to each other, thereby applying force and/or torque to the at least one pair of coupling-members, wherein the instrument-interface is provided in a sterile section of the trajectory-guide, and the actuator-interface is provided in a non-sterile section of the trajectory-guide, and wherein the trajectory-guide further comprises a baffle-member separating the sterile section from the non-sterile section, and a sterility-sleeve attached to the baffle-member;
- the actuator-unit having two or more engaging-members adapted to releasably engage and hold the actuator-interface of the trajectory-guide at the two or more separate locations, and to apply a force and/or torque to the trajectory-guide by moving the two or more engaging-members with respect to each other, wherein the actuator-unit further comprises a sensor-unit that senses a) whether a trajectory-guide is placed with respect to the actuator-unit in a manner that allows the engaging-members to accurately engage the actuator-interface, and particularly b) whether the engaging-members have accurately engaged the actuator-interface; and
- a retainer-receptacle adapted to temporarily accommodate the trajectory-guide, and to restrain flexibility of the trajectory-guide while it is accommodated.

In general, the inventive frontend-system includes three major components which can be considered as separate inventions without reference to any of the two other major components. Thus, even though the three major components are described in the following in the context of a combined frontend-system, each of these components and the features assigned to the respective component, which will be described in the following, can be considered to represent an invention of its own.

Trajectory-Guide

The first inventive component of the frontend-system is represented by a flexible trajectory-guide comprising at least one pair of force- and/or torque transmitting coupling-members that act, in an opposed manner, on an instrument-interface adapted to hold a medical instrument, thereby adjustably coupling the instrument-interface to an actuator-interface adapted to be releasably engaged and held by an actuator unit at two or more separate locations which are movable with respect to each other, thereby applying force and/or torque to the at least one pair of coupling-members, wherein the instrument-interface is provided in a sterile section of the trajectory-guide and the actuator-interface is provided in a non-sterile section of the trajectory-guide, and wherein the trajectory-guide further comprises a baffle-member separating the sterile section from the non-sterile section, and a sterility-sleeve attached to the baffle-member.

In other words, the baffle-member and the sterility-sleeve form an impermeable barrier between the sterile section and the non-sterile section of the trajectory-guide. Consequently, the only passage from the non-sterile section to the sterile section is through the distant end of the sterility-sleeve which, as will be described further below, will come to rest at a proximal section of a support arm. Thus, the sterility-sleeve may have a substantially tubular form. In the alternative, however, it is also conceivable that the sterility-sleeve is attached to the baffle-member via releasable or non-releasable fasteners which however have to be adapted to preserve sterility and must not allow contaminants to pass through between the sterility-sleeve and the baffle-member.

Further, the inventive trajectory-guide may comprise an instrument-interface which holds an elongated medical instrument so that the instrument can be moved relative to the instrument-interface along its longitudinal axis only, and an adjustment section coupling the instrument-interface to an actuator-interface via which the trajectory-guide is attached to a support structure. The instrument-interface is coupled to the actuator-interface and therefore also to the support structure via one or more flexible beam members which can be deflected so as to move the instrument-interface together with the instrument relative to the support structure, allowing the longitudinal axis of the elongated instrument to be adjusted with respect to the support structure. Further, the trajectory-guide comprises one or more pairs of coupling members which are connected to at least one of the beam members and which are used to apply force and/or torque on the beam members, which in turn causes the beam member(s) to bend or at least move. Each of the coupling members further comprises an interface connecting the coupling member to an actuator by means of which the beam member(s) can be flexed. Further, the beam member(s) themselves may comprise an interface via which it is/they are connected to the support structure or even to a further actuator employed to move the beam member with respect to the support structure, thereby allowing further adjustment of the instrument-interface with respect to the support structure.

The adjustable trajectory-guide comprises at least one pair of coupling members which act on the first end of at least one beam member in an opposed manner, and which are in particular coupled to the same section of the actuator-interface. With each pair of coupling members acting in an opposed manner, the beam member can be flexed in two opposed directions, which will double the possible scope of adjustment. In case the two opposed coupling members are coupled to one and the same engagement interface, it is possible to cause the beam member to bend in two opposed directions by employing only one actuator.

Further, the trajectory-guide may have a symmetrical shape, with the longitudinal axis of the beam member being the symmetrical axis. With regard to the coupling members, a symmetrical shape of the trajectory-guide will cause the beam member to bend in the two opposite directions in exactly the same manner, possibly caused by one single actuator which may act in two opposite directions.

Further, the at least one beam member may have at least one dedicated direction of flexibility. This can be achieved by a suitable cross sectional shape of the beam member providing an increased stiffness of the beam member in any direction which differs from the one or more dedicated bending directions. In the context of the at least one flexible beam member, the term "flexible" may on the one hand mean that a beam member may have a main body portion that is deformable itself, i.e. that will change its shape, particularly will bend or flex upon appliance of an external force. On the other hand however, a "flexible" beam member may also be a beam member with a relatively unflexible body portion that will maintain its shape at least sectionwise, but which is provided with one or more flexible sections or hinges that allow the beam member to deflect with respect to other structures it is attached to via the flexible sections or hinges.

The inventive trajectory-guide may further comprise at least one spacer between a beam member and a coupling member, which is adapted to maintain a clearance between the beam member and the coupling member. Such spacers will prevent the coupling members from any unintended deflection with respect to the beam member that may result in an increased amount of force or torque that has to be applied on the beam member for a certain amount of flexion. The spacers further prevent any unintended movement of the coupling members with respect to the beam member which may result in an unintended deflection of the instrument-interface. The spacers also provide a certain guiding for the coupling members while they transmit force and/or torque from the actuators to the beam member.

Further, at least one coupling member may be connected to a beam member at an acute angle at the beam member's first end. This results in a rather prominent position of the instrument-interface with respect to the trajectory-guide, which in turn allows a free and unobstructed access to the medical instrument held by the instrument-interface.

It is conceivable that at least one actuator-interface and the instrument-interface are provided at opposite sides of the trajectory-guide, particularly with the beam member positioned between the actuator-interface and the instrument-interface. In other words, the instrument-interface, the beam member and the actuator-interface are arranged in line, with the at least one actuator-interface and the corresponding actuators positioned away from the instrument-interface. Again, this will result in a most prominent and accessible position of the medical instrument held by the instrument-interface.

The instrument-interface may have a third interface adapted to provide a connection to a support structure holding the instrument-interface, the third interface being provided at a location which is spaced from a location where a beam member of the adjustment section is connected to the instrument-interface. Assuming that the support structure holds the third interface in a fixed spatial position (i.e. fixed location and orientation), any motion of the beam member including a flexion of a beam member, will cause the point where the beam member is connected to the instrument-interface to move with respect to the point where the third interface is connected to the instrument-interface. In the end, this will result in an altered alignment of the instrument-interface together with the longitudinal axis of the medical instrument.

In the alternative, the trajectory-guide may comprise two adjustment sections as described above, wherein the beam members of the two adjustment sections are connected to the instrument-interface at locations spaced apart from each other. Assuming that the two adjustment sections can be actuated independently from each other, the alignment of the instrument-interface together with the longitudinal axis of the medical instrument can be varied in an arbitrary manner over a wide range.

Even though it is conceivable that the two adjustment sections are connected to the instrument-interface at arbitrary positions, it is preferred to provide two, particularly two identical adjustment sections arranged relative to each other in a congruent, particularly in a symmetrical manner. This will not only allow for simplifying the manufacturing process of the trajectory-guide, but again also allows for a prominent position of the instrument-interface.

It is further conceivable that at least one, preferably both adjustment sections are connected to the instrument-interface via joints, in particular flexible film joints. Such joints will provide for a determined movement of the instrument-interface with respect to the corresponding adjustment section, wherein the movement is restricted to the degree(s) of freedom allowed by the joint(s). Any type and number of joints may be provided for the connection between an adjustment section and the instrument-interface. In a specific embodiment, each of the adjustment sections may be connected to the instrument-interface via a pair of flexible film joints that each allow for a rotational degree of freedom and which, for each adjustment section, are aligned perpendicularly relative to each other.

It is further conceivable that the trajectory-guide is made from a radiolucent material, particularly from a plastic material which is at least in part injection molded or extruded, specifically wherein the trajectory-guide is formed as one integrally formed part. In case the trajectory-guide is formed as one integrally formed part, the spacers which are hinged attached to the beam member and to a corresponding coupling member may be attached via at least one integral hinge. With the adjustment sections being arranged in a congruent manner as explained above, it is possible to form the trajectory-guide at least in part by an extrusion process.

The trajectory-guide may be provided as a disposable, pre-sterilized and packaged product. In this case, the trajectory-guide may be attached to the support structure prior to a medical procedure, and can be discarded after use, so that no additional sterilization process is necessary.

Actuator-Unit

The second inventive component relates to an actuator-unit having two or more engaging members adapted to releasably engage and hold, in a manner described herein, the actuator-interface of the trajectory-guide at two or more separate locations, and to move the two or more engaging-members with respect to each other, wherein the actuator-unit further comprises a sensor-unit that senses a) whether a trajectory-guide as described herein is placed with respect to the actuator-unit in a manner that allows the engaging members to accurately engage the actuator-interface, and particularly b) whether the engaging-members have accurately engaged the actuator-interface.

In other words, the inventive actuator-unit has at least one of the two engaging-members connected to an actuator so as to cause a movement of the two engaging-members with respect to each other. In one specific embodiment the actuator may be a linear motor.

Further, the sensor-unit may comprise one or more sensors that are adapted to recognize whether a trajectory-guide is fully inserted into the actuator-unit. This task could be for example realized by utilizing a distance sensor, a push-button, a light-barrier or any other sensor suitable to measure the position of the trajectory-guide during insertion into the actuator-unit and/or whether the trajectory-guide has reached a desired final position. As soon as the trajectory-guide has been correctly inserted into the actuator-unit, sensed, for example, by the sensor, a clamping mechanism may, for example, fully automatically and without any manual interaction of personnel, cause the engaging-members to engage the corresponding interfaces of the trajectory-guide. In this context, the sensor-unit may sense via one or more suitable sensors, whether the clamping force increases during clamping in an expected manner, or reaches an expected amount, and/or whether the clamping-forces measured via separate sensors are "symmetric". This is because opposed clamping components are expected to experience the same reaction force during clamping. Thus, the sensor-unit may also provide for a verification whether the trajectory-guide has been correctly engaged by the actuator unit.

Retainer-Receptacle

A third component being inventive by itself is represented by a retainer-receptacle that is adapted to temporarily accommodate a trajectory-guide, and to restrain flexibility of the trajectory-guide while it is accommodated.

In other words, the retainer-receptacle comprises one or more portions, particularly on it's surface, that are formed to "match" corresponding parts of the trajectory-guide. Thus, the retainer-receptacle provides a "corset" for the generally flexible and therefore unstable trajectory-guide. By being "tied" by the retainer-receptacle, the trajectory-guide maintains its shape and can therefore be easily handled, for example during insertion into an actuator-unit.

Further Aspects

In the following, further aspects of the present invention are described in the context of preferred embodiments. It is however to be noted that the features described in the following may be contained in the sterility-preserving robotic frontend-system, but may as well be contained in any one of the three above described components to which it is assigned.

In a first embodiment, the trajectory-guide may be provided as one single integral part. Further, the baffle-member may seal one end of the substantially tubular sterility-sleeve. As already described above, this prevents any contaminance from passing the barrier which is formed by the baffle-member and the sterility-sleeve in the vicinity of the trajectory-guide.

According to a further embodiment, the actuator-unit comprises a user-interface that outputs at least one of a haptic, a visual and an acoustic signal relating to the state of engagement between the actuator-interface and the two or more engaging members.

In other terms, the user is provided with a feedback during setup of the frontend-system. For example, the user-interface may comprise a red, a yellow and a green light, wherein a red light indicates that no trajectory-guide is inserted, a yellow light indicates that a trajectory-guide is inserted into the actuator-unit, but is not properly attached to it yet, and a green light indicates that the actuator-unit has properly engaged the trajectory-guide, such that the user may proceed with the further setup of the frontend-system. Additionally or alternatively, the user-interface may also output sound-signals indicating whether or not the trajectory-guide has been properly installed.

As it has been already indicated above, the actuator-unit may be coupled to an adjustable support, that is capable of holding the actuator unit at a spatially fixed position. Further, the support may be robotic arm, particularly a semi-robotic arm, wherein the actuator-unit is provided at a distal end of the robotic arm.

As to the retainer-receptacle, it has to be noted that the receptacle may be used for both, sterile or unsterile transport of the trajectory-guide, and as a positioning-aid for the otherwise unstable trajectory-guide. For this purpose, the retainer-receptacle may fasten at least to the sterile section of the trajectory-guide, thereby at least partially accommodating the sterile section. More specifically, the retainer-receptacle may fasten to the trajectory-guide via a form-fit, particularly via a press-fit, and specifically fits tightly around the accommodated part of the trajectory-guide.

For a fast and easy placement of a trajectory-guide with a sterility-sleeve attached to it, the retainer-receptacle may further be adapted to hold the sterility-sleeve in place, as well. For this purpose, a circumferential holding-section may be provided, that may run around a fastening-section where the trajectory-guide is fastened and held in place by the retainer-receptacle.

Since the retainer-receptacle may be made from a plastic material, it is conceivable that it is die-cast or made from a three-dimensionally formed sheet having a substantially constant thickness.

According to a further embodiment of the invention, the retainer-receptacle further comprises a gripping-section adapted to be grasped by a person, thus acting as a handle, and wherein the gripping-section and a fastening-section engaging the accommodated trajectory-guide are in particular arranged on opposite sides of the retainer-receptacle, particularly with the holding-section being arranged between the gripping-section and the fastening-section. By arranging the holding-section with the sterility-sleeve being stored there, between the gripping-section and the fastening-section of the retainer-receptacle, any "cross-border" interaction is avoided. This means, for example, that a sterile person does not need to interact with a possibly unsterile support structure, as the trajectory-guide will be "gripped" by the actuator-unit fully automatically.

According to a further embodiment that has been already described further above, the trajectory-guide and the retainer-receptacle are provided as disposable sterile components, whereas the actuator-unit is provided as a reusable non-sterile component.

A further aspect of the present invention relates to a packaging-container having an inner sterile volume containing the retainer-receptacle and the trajectory-guide according to one of the embodiments described herein, wherein the retainer-receptacle is fastened to the trajectory-guide to form a combined fitting that can be one-handedly taken out of the packaging-container as one single part. Since a sterile person exclusively comes into contact with the gripping-section of the retainer-receptacle during unpacking of the trajectory-guide and inserting the trajectory-guide into the actuator-unit, whereupon the trajectory-guide is automatically engaged by the actuator-unit, sterility can be preserved during setup of the frontend-system in the most convenient manner.

A further aspect of the present invention relates to a corresponding method of setting up a sterility-preserving robotic frontend-system, comprising the following steps:

- providing a actuator-unit and a sterile packaging-container according embodiments described herein;
- opening the packaging-container by non-sterile personnel;
- grasping the gripping-section of the retainer-receptacle and removing the combined fitting comprising the retainer-receptacle and the trajectory-guide from the packaging-container by sterile personnel;
- positioning the combined fitting with respect to the actuator-unit by sterile personnel, thereby allowing the engaging-members to automatically engage and hold the actuator-interface in an accurate manner;
- covering the actuator-unit and the support with the sterility-sleeve by sterile personnel;
- releasing the retainer-receptacle from the trajectory-guide by sterile personnel. After the trajectory-guide has been installed within the actuator-unit, the actuator-unit and the support may be covered with the sterility-sleeve by pulling the sterility-sleeve, which is initially held in place by the retainer-receptacle in a packed manner, from the retainer-receptacle over the actuator-unit and the support towards the proximal end of the support.

BRIEF DESCRIPTION OF THE DRAWINGS

In the following, the invention is described with reference to the enclosed figures which represent preferred embodiments of the invention. The scope of the invention is however not limited to the specific features disclosed in the figures, which show:

FIG. 1 the inventive retainer-receptacle shown from two sides;

FIG. 2 the inventive actuator-unit being accommodated in the inventive retainer-receptacle;

FIG. 3 placing the trajectory-guide together with the retainer-receptacle into the inventive actuator-unit;

FIG. 1 shows a preferred embodiment of the inventive retainer-receptacle 3 that is formed as one single integral part by being die-cast. The receptacle 3 features a central recess that has a shape corresponding to a trajectory-guide 1 that will be installed later within the recess, so that the trajectory-guide 1 is held firmly in place and will maintain its shape as long as it is accommodated within the retainer-receptacle 3. At the bottom of the recess, a form-fit for the inserted trajectory-guide 1 is provided by a fastening-section 16 comprising two opposing noses that engage both of the opposed openings of the tubular instrument-interface 5 of the trajectory-guide 1.

Figure 4:
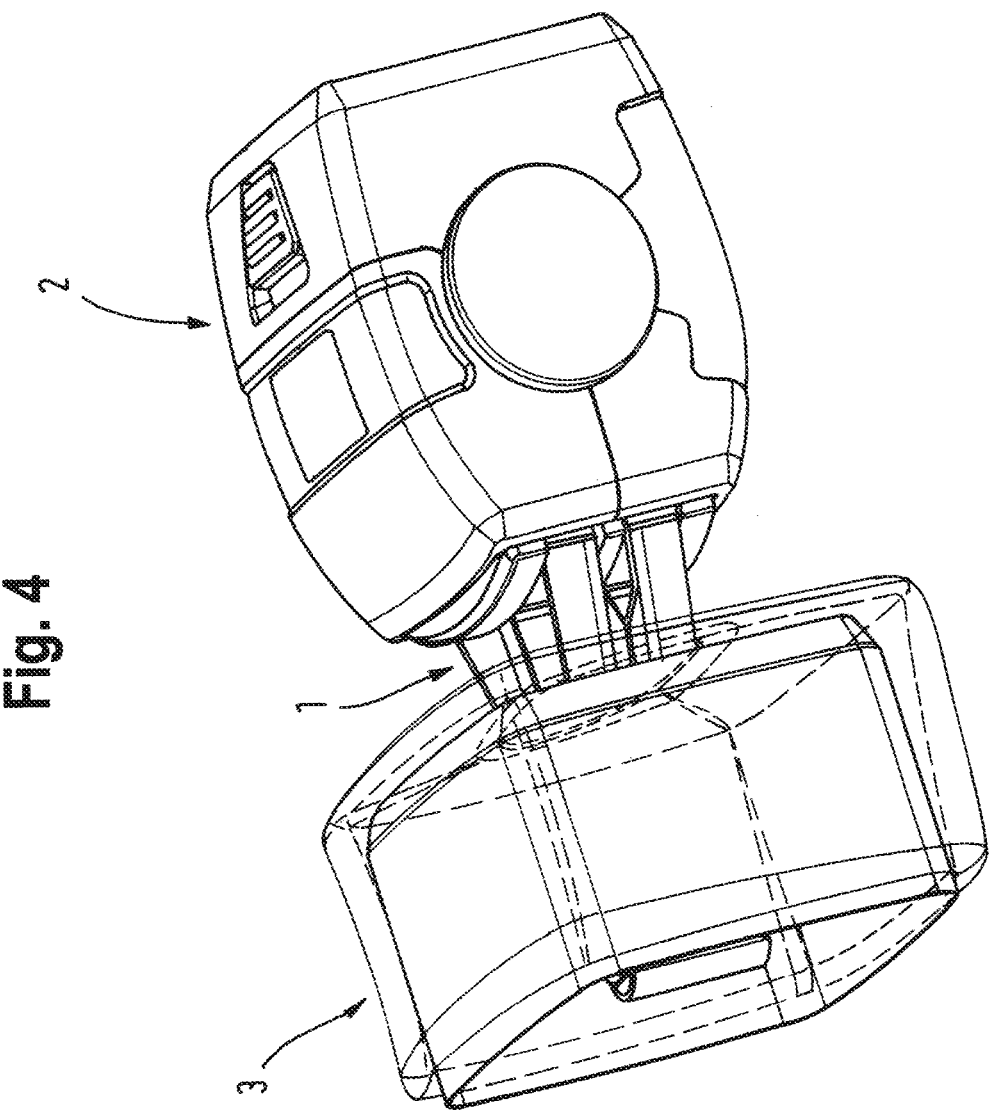
FIG. 4 the trajectory-guide being installed in the actuator-unit with the retainer-receptacle still in place.

The recess provided on one of the receptacle 3 forms at the same time a gripping section 17 on the other side of the receptacle 3, which can be grasped by a person for handling the receptacle 3 together with the trajectory-guide 1. At the circumference of the receptacle 3 a substantially ring-shaped holding-section 15 is provided onto which the sterility-sleeve 11 of the trajectory-guide 1 is stored during transport and may be removed therefrom to cover the unsterile components of the frontend-system.

FIG. 2 shows the inventive trajectory-guide 1 being accommodated in the retainer-receptacle 3, with the sterility-sleeve 11 being stored on the holding-section 15.

The trajectory-guide 1 basically comprises a tubular instrument-interface 5 that is connected to an actuator-interface 7 comprising, in this specific embodiment, three different interfaces for corresponding engaging-members 12 of an actuator-unit 2. The instrument-interface 5 is connected to the actuator-interface 7 via a flexible beam-member (not indicated) which is described in more detail further above. By means of coupling-members 4 which act from different sides on the beam-member and therefore also on the instrument-interface 5, the instrument-interface 5 can be adjusted with respect to the actuator-unit 2 by moving the different sections of the actuator-interface 7 with respect to each other. Moving one of the engaging-sections of the actuator-interface 7 will cause the coupling-members 4, which are attached to this section, to pull at the distal end of the beam-member, thereby causing the instrument-interface 5 attached thereto to move in a corresponding way. In the shown embodiment of the trajectory-guide 1, the coupling-members 4 are adapted to transmit pulling forces only, wherein the trajectory-guide 1 comprises two rather identical adjustment sections which have been described further above in more detail, as well.

Figure 5:
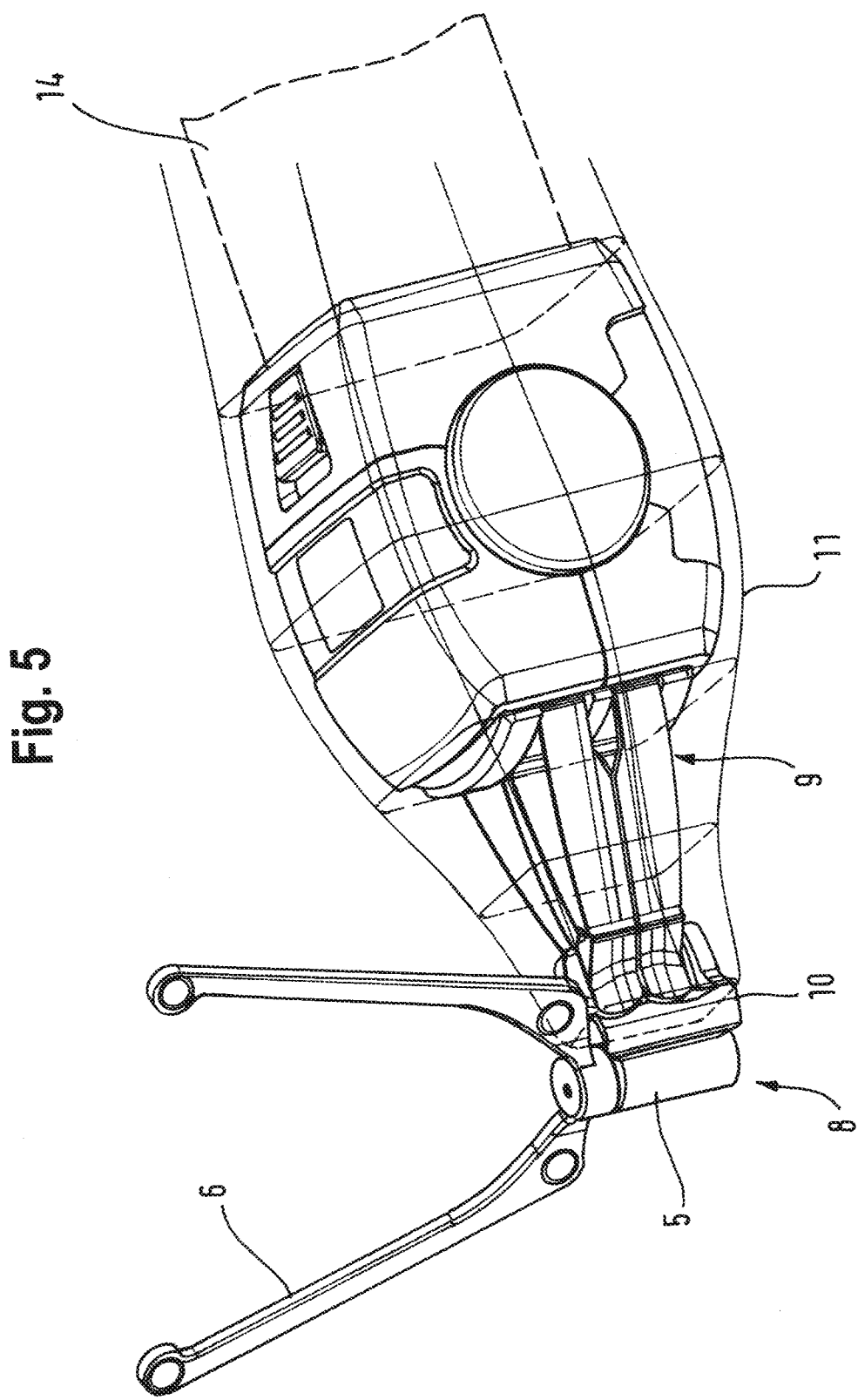
FIG. 5 the trajectory-guide being installed and in an operative state.

A baffle-member 10 is provided between the instrument-interface 5 forming the sterile part 8 of the trajectory-guide 1, and the remaining parts of the trajectory-guide 1 which are considered here as the unsterile part 9 (in this respect, please also refer to FIG. 5).

FIG. 3 shows the trajectory-guide 1 being held by the retainer-receptacle 3 in the manner that has already been shown in FIG. 2 and it becomes apparent therefrom how the retainer-receptacle 3 holding the trajectory-guide 1 is approaching an actuator-unit 2 being held at the distal end of a support arm (not shown in FIG. 3). The actuator-unit 2 has two slots into which the corresponding adjustment-sections of the trajectory-guide 1 will enter the actuator-unit 2, wherein an engaging-member 12 will come to rest within a corresponding section of the actuator-interface 7 (being symmetric to another upper section indicated by reference sign 7 in FIG. 3). The remaining engaging-members 12 that cannot be seen in FIG. 3 will engage the corresponding sections of the actuator-interface 7, as well. After the trajectory-guide 1 has been correctly placed in the actuator-unit 2, a sensor-unit 13 (not shown in full detail) causes the engaging-members 12 to fully engage the corresponding sections of the actuator-interface 7. The state of engagement will be shown to the user via interface 20 comprising a display.

FIG. 4 shows the trajectory-guide 1 being fully installed in the actuator-unit 2, wherein the retainer-receptacle 3 is still present at the distal portion of the trajectory-guide 1.

After having pulled off the retainer-receptacle 3 from the trajectory-guide 1, and after the sterility-sleeve 11 has been pulled off from the holding-section 15 in a proximal direction over the unsterile components including the support arm 14, the inventive frontend-system is fully set up and ready for use as shown in FIG. 5. An instrument 6 (here a bifurcated tracking marker array) may be held and guided via the sterile instrument-interface 5, thereby being shielded from the unsterile parts of the frontend-system.

Figure 6:
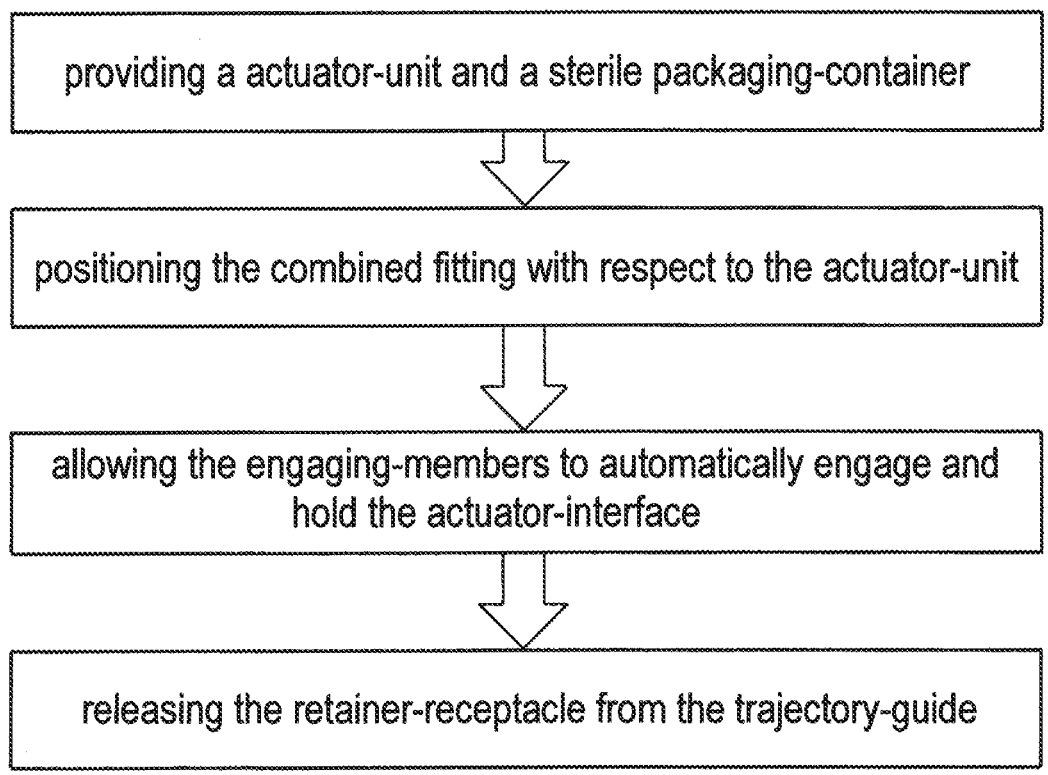
FIG. 6 the basic steps of the inventive method.

FIG. 6 merely shows the basic steps of a specific embodiment a method according to the present invention, for setting up a sterility-preserving robotic frontend-system.

The invention claimed is:

1. A system comprising:
    a flexible trajectory-guide comprising:
        an unsterile section comprising an actuator-interface adapted to be releasably engaged and held by two or more engaging members at two or more separate sections that are movable with respect to each other;
        a sterile section comprising an instrument-interface adapted to hold a medical instrument;
        a pair of force- or torque-transmitting coupling-members arranged opposite each other and adjustably coupling the instrument-interface to the actuator-interface, such that the instrument-interface is configured to be postionally adjusted with respect to an actuator unit by moving the two or more separate sections of the actuator-interface with respect to each other;
        a baffle-member separating the unsterile section from the sterile section; and
        a sterility sleeve attached to the baffle-member;
    the actuator unit comprising:
        two or more engaging-members adapted to releasably engage and hold the actuator-interface of the flexible trajectory-guide at the two or more separate sections and to apply a force or torque to the flexible trajectory-guide; and
        a sensor-unit, which senses:
            a) whether the flexible trajectory-guide is placed with respect to the actuator unit in a manner allowing the engaging-members to accurately engage the actuator-interface; and
            b) whether the engaging-members have accurately engaged the actuator-interface; and
    a retainer-receptacle adapted to fasten to the sterile section of the flexible trajectory-guide, the retainer-receptacle comprising a circumferential holding-section that runs around a fastening-section of the retainer-receptacle.

2. The system according to claim 1, wherein the trajectory-guide is provided as one single integral part.

3. The system according to claim 1, wherein the retainer-receptacle fastens to the flexible trajectory-guide via a form fit.

4. The system according to claim 1, wherein the retainer-receptacle is die-cast or made from a three-dimensionally formed sheet having a substantially constant thickness.

5. The system according to claim 1, wherein the retainer-receptacle further comprises:
    a gripping-section comprising a first area of the retainer-receptacle adapted to be grasped by a person;
    a holding-section comprising a second area of the retainer-receptacle adapted to hold the sterility sleeve; and
    a fastening-section comprising a third area of the retainer-receptacle adapted to fasten to the sterile section of the flexible trajectory-guide,
    the first and third areas being arranged on opposite sides of the retainer-receptacle and the second area being arranged between the first and third areas.

6. The system according to claim 1, wherein the flexible trajectory-guide and the retainer-receptacle are disposable sterile components, and the actuator-unit is a reusable non-sterile component.

* * * * *